United States Patent [19]

Pedain et al.

[11] Patent Number: 5,064,960

[45] Date of Patent: Nov. 12, 1991

[54] SOLUTIONS OF ISOCYANURATE POLYISOCYANATES IN COATINGS SOLVENTS AND A PROCESS FOR THEIR PRODUCTION

[75] Inventors: Josef Pedain, Cologne; Dieter Margotte, Krefeld, both of Fed. Rep. of Germany

[73] Assignee: Bayer Aktiengesellschaft, Leverkusen, Fed. Rep. of Germany

[21] Appl. No.: 571,465

[22] Filed: Aug. 22, 1990

[30] Foreign Application Priority Data

Aug. 29, 1989 [DE] Fed. Rep. of Germany ....... 3928503

[51] Int. Cl.$^5$ .............................. C07D 251/02
[52] U.S. Cl. .................................. 544/222; 544/221
[58] Field of Search .......................... 544/221, 222

[56] References Cited

U.S. PATENT DOCUMENTS 3,996,223 12/1976 Gupta et al. ............... 260/248

FOREIGN PATENT DOCUMENTS 1458564 12/1976 European Pat. Off. .

*Primary Examiner*—Johann Richter
*Attorney, Agent, or Firm*—Joseph C. Gil; Thomas W. Roy

[57] ABSTRACT

The present invention relates to a process for the preparation of a composition containing an isocyanurate polyisocyanate dissolved in a solvent inert to isocyanate groups by a) reacting 2.5 to 7% of the isocyanate groups of a starting diisocyanate based on 2,4-diisocyanatotoluene or a mixture of 2,4-diisocyanatotoluene and 2,6-diisocyanatotoluene with a monohydric alcohol corresponding to the formula

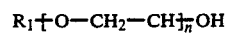

$$R_1 + O-CH_2-CH \cdot_n OH$$
$$R_2$$

wherein
  $R_1$ is an aliphatic or cycloaliphatic $C_{6-18}$ hydrocarbon radical which may be olefinically unsaturated,
  $R_2$ is hydrogen or a methyl group, and
  n is 0 or an integer from 1 to 3, b) adding a sufficient amount of an organic solvent which is inert to isocyanate groups to form a 30 to 70% solution of the urethanized diisocyanate either before, during or after step a), c) subsequently partially trimerizing the remaining isocyanate groups of said urethanized diisocyanate in the presence of a catalyst which accelerates the trimerization of isocyanate groups and d) terminating the trimerization reaction when the content of unreacted diisocyanotoluene is less than 0.5% by weight by the addition of a catalyst poison.

The present invention also relates to the solutions of isocyanurate polyisocyanates obtained by this process.

12 Claims, No Drawings

SOLUTIONS OF ISOCYANURATE POLYISOCYANATES IN COATINGS SOLVENTS AND A PROCESS FOR THEIR PRODUCTION

BACKGROUND OF THE INVENTION

1. Field of the Invention

This invention relates to a new process for the production of solutions of isocyanurate polyisocyanates based on diisocyanatotoluenes in solvents inert to isocyanate groups. The solutions according to the invention possess improved dilutability with aromatic solvents. The invention also relates to the solutions of isocyanurate polyisocyanates produced by this process.

2. Description of the Prior Art 2,4- and 2,6-diisocyanatotoluene, especially mixtures of these two diisocyanates, are important industrial raw materials and and may be used in a wide variety of applications such as in paints and coating compositions. As paint resins, they are used inter alia in the form of derivatives or adducts containing urethane or isocyanurate groups.

The isocyanurate polyisocyanates based on 2,4- and optionally 2,6-diisocyanatotoluene are valuable components for o two-component polyurethane coatings for wood and furniture. The modified polyisocyanates are generally produced by the partial trimerization of the isocyanate groups of 2,4- and optionally 2,6-diisocyanatotoluene in 30 to 70% by weight solutions in suitable paint solvents (cf. for example DE-OS 2 414 413). To produce ready-to-use paints, the resulting solutions are often combined with solutions of fatty acid-modified hydroxyl polyesters in toluene, xylene or mixtures of these solvents with petroleum fractions. However, due to the limited compatibility of the polyisocyanate solutions with weakly polar solvents or with hydroxyl group-containing binder components dissolved in such solvents, incompatibilities can readily occur and are reflected in are reflected in haziness and in precipitation which restrict the usefulness of the polyisocyanate solutions.

Accordingly, an object of the present invention is to provide a new process for the production of solutions of isocyanurate polyisocyanates based on 2,4- and optionally 2,6-diisocyanatotoluene which results in solutions having improved dilutability with weakly polar solvents and, in particular, improved dilutability with aromatic solvents.

This object may be achieved in accordance with the present invention by the partial urethanization of the diisocyanatotoluenes used as starting diisocyanates with substoichiometric quantities of certain alkanols optionally containing ether groups and by subsequent partial trimerization of the urethanized starting diisocyanates in the form of 30 to 70% by weight solutions in paint solvents until the content of unreacted starting diisocyanate in the solutions has fallen to below 0.5% by weight.

It is known that 2,4- and, optionally, 2,6-diisocyanatotoluene could be modified by partial urethanization of the isocyanate groups and partial trimerization of the isocyanate groups in order to obtain special effects.

Thus, DE-OS 2 414 413 describes the reaction of solutions of isocyanurate polyisocyanates and considerable quantities of monomeric starting diisocyanatein in paint s solvents with alkanols optionally containing ether groups in order to reduce the content of monomeric starting diisocyanates to less than 0.7% by weight, based on solids, by substantially selective urethanization thereof. Accordingly, the main difference between this process and the process according to the invention, which is described in detail hereinafter, lies in the sequence of the reactions. According to the invention, the trimerization step follows the urethanization step whereas, according to DE-OS 2 414 413, the urethanization step follows the trimerization step for a totally different purpose, i.e., to reduce the content of unreacted monomeric starting diisocyanates.

In the process according to DE-OS 2 452 532, the partial trimerization of the isocyanate groups of aromatic diisocyanates, particularly diisocyanatotoluenes, is carried out using a binary catalyst system based on Mannich bases and carbamic esters of isocyanates and alcohols containing secondary hydroxyl groups. The carbamic acid esters may be formed, for example, in situ by the partial urethanization of the isocyanate groups of the starting diisocyanate with certain secondary alcohols. In practice, this means that the isocyanate groups are first subjected to partial urethanization and then to partial trimerization. The reaction sequence thus corresponds to the reaction sequence of the process according to the invention described in detail hereinafter. The secondary alcohols mentioned in the prior publication also include adducts of propylene oxide with higher alkanols, such as for example 1-decanol or 1-octadecanol. However, these alcohols are evidently not preferred starting materials because simple secondary alcohols [such as bis-(2-hydroxypropyl)-ether] or adducts of propylene oxide with simple polyhydric alcohols (such as propylene glycol or trimethylol propane) are used in the examples. Secondary alcohols are not among the preferred alcohols for the process according to the invention.

The main difference between the process according to the present invention and the process according to DE-OS 2 452 532 lies in the totally different problem and in the different solution to that different problem. The problem addressed by the invention according to DE-OS 2 452 532 was to provide a process for the partial trimerization of the isocyanate groups of the starting diisocyanates which did not depend upon the use of catalyst poisons and which could readily be controlled by the temperature profile and the quantity of catalysts used. The solution to this problem was the use of the binary catalyst systems for the trimerization of the starting diisocyanates in in order and termination of the trimerization at the particular degree of trimerization required by an increase in temperature unimpeded by any solvents. It is clear that prior publication directed to this process does not teach or suggest the solution to the problem addressed by the present invention.

SUMMARY OF THE INVENTION

The present invention relates to a process for the preparation of a composition containing an isocyanurate polyisocyanate dissolved in a solvent inert to isocyanate groups by a) reacting 2.5 to 7% of the isocyanate groups of a starting diisocyanate based on 2,4-diisocyanatotoluene or a mixture of 2,4-diisocyanatotoluene and 2,6-diisocyanatotoluene with a monohydric alcohol corresponding to the formula

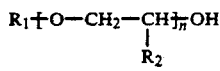

wherein
- R₁ is an aliphatic or cycloaliphatic $C_{6-18}$ hydrocarbon radical which may be olefinically unsaturated,
- R₂ is hydrogen or a methyl group, and
- n is 0 or an integer from 1 to 3, b) adding a sufficient amount of an organic solvent which is inert to isocyanate groups to form a 30 to 70% solution of the urethanized diisocyanate either before, during or after step a), c) subsequently partially trimerizing the remaining isocyanate groups of said urethanized diisocyanate in the presence of a catalyst which accelerates the trimerization of isocyanate groups and d) terminating the trimerization reaction when the content of unreacted diisocyananotoluene is less than 0.5% by weight by the addition of a catalyst poison.

The present invention also relates to the solutions of isocyanurate polyisocyanates obtained by this process.

DETAILED DESCRIPTION OF THE INVENTION

Starting materials for the process according to the invention are 2,4-diisocyanatotoluene or mixtures thereof with 2,6-diisocyanatotoluene. The isomer mixtures are preferably used in a ratio by weight of 2,4-isomer:2,6-isomer of 3:2 to 9:1, more preferably 3.9:1 to 4.1:1.

At least the second stage of the process according to the invention is carried out in the presence of paint solvents inert to isocyanate groups. These paint solvents include ethyl acetate, butyl acetate, methyl ethyl ketone, methyl isobutyl ketone, methoxypropyl acetate and mixtures of such solvents.

In the first stage of the process according to the invention 2.5 to 7%, preferably 3 to 5%, of the isocyanate groups of the starting diisocyanates are reacted with a monohydric alcohol or with a mixture of monohydric alcohols described below.

Suitable monohydric alcohols are those corresponding to the formula

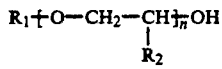

wherein
- R₁ is an unsaturated aliphatic or cycloaliphati $C_{6-18}$ hydrocarbon radical which may be olefinically unsaturated, preferably a saturated alipha $C_{8-12}$ hydrocarbon radical,
- R₂ is hydrogen or a methyl group, preferably hydrogen, and
- n is 0 or an integer from 1 to 3, preferably 0.

Examples of suitable monohydric alcohols are 1-hexanol, cyclohexanol, 1-octanol, 2-ethyl-1-butanol, 2-ethyl-1-hexanol, 4-methyl-2-pentanol, 1-decanol, 1-dodecanol, 1-tetradecanol, stearyl alcohol, 9-octadecen-1-ol, the ethoxylation and/or propoxylation products of these alcohols corresponding to the above formula and mixtures of such alcohols. 2-ethyl-1-hexanol is particularly preferred as the monohydric alcohol.

The first stage of the process according to the invention comprises the partial urethanization of the isocyanate groups of the starting diisocyanate with the alcohol component. 2.5 to 7%, preferably 3 to 5%, of the isocyanate groups of the starting diisocyanates are urethanized by reaction with the monohydric alcohol or with a mixture of monohydric alcohols. This modification of the diisocyanate with the monoalcohols is carried out at approximately 0 to 120° C., preferably 20 to 80.C, either in the presence or the absence of the paint solvents previously discussed. After the urethanization step, these solvents serve as reaction medium for the partial trimerization step. When the urethanization step is carried out in the absence of solvents, the partly urethanized starting diisocyanates are dissolved in a solvent or solvent mixture before the trimerization step.

The subsequent partial trimerization of the isocyanate groups is carried out in the presence of a catalyst at 20 to 80° C. using 30 to 70% by weight solutions of the partly urethanized starting diisocyanates.

Any of the known trimerization catalysts such as phosphines, alkali salts, alkali alcoholates, tertiary amines and the like, may be used as the trimerization cataysts. However, Mannich bases of the type disclosed in DE-OS 2 452 532 are preferably used as the trimerization catalysts. The trimerization reaction is continued until the content of monomeric starting diisocyanate in the reaction mixture, which is free from urethane groups and isocyanurate groups, has fallen to below 0.5% by weight, based on solution. This substantially corresponds to the trimerization of 40 to 60% of the isocyanate groups present after the urethanization step.

The trimerization reaction is terminated by the s addition of a catalyst poison. Suitable catalyst poisons include sulfur (when phosphines are used as catalysts); substances showing an acidic reaction (when alkali salts, alkali alcoholates or tertiary amines are used as catalysts); and alkylating agents such as toluene sulfonic acid methyl ester (when the preferred Mannich bases are used as catalysts).

The solutions of isocyanurate polyisocyanates obtained as the end products of the process according to the invention have an NCO content of 8 to 17% by weight, based on solids. The solutions are distinguished in particular by improved dilutability with weakly polar solvents of the type mentioned above, especially improved dilutability with aromatic solvents such as toluene or xylene. The solutions also have better compatibility with the hydroxyl group-containing reactants conventionally used in combination with the isocyanurate polyisocyanates, especially fatty acid-modified polyesters, polyacrylate resins containing hydroxyl groups and cellulose acetobutyrates containing hydroxyl groups.

In the following examples, all parts and percentages are by weight unless otherwise indicated.

In the following examples, a 40% by weight solution in xylene of a Mannich base corresponding to the following formula

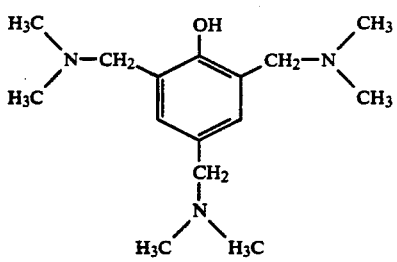

is used as the Catalyst solution.

EXAMPLE 1 ACCORDING TO THE INVENTION 375.5 g of a mixture of 2,4- and 2,6-diisocyanatotoluene in a ratio of 4:1 were mixed with 19.8 g 2-ethyl hexanol at 23° C. and the resulting mixture was heated with stirring for 4 hours to 50° C. The NCO content of the liquid fell to 44.1%. 3.5% of the NCO groups present were consumed. The liquid was then dissolved in 380 g butyl acetate and 0.75 g of the catalyst solution was added. The trimerization reaction began immediately; the temperature of the solution was kept at 75° C. by cooling. After intervals of 3 to 4 hours, another 0.75 g catalyst solution was added, in all, three times. The reaction was over after about 30 hours. To inactivate the cataylst, 1 g toluene sulfonic acid methyl ester was added and the reaction mixture was heated for 1 hour to 100° C. A clear colorless solution having the following properties was obtained:
concentration—approx. 50%,
viscosity—1,000 mPa.s/23° C.,
NCO content—7.8%,
free diisocyanate—0.25%.

EXAMPLE 2 ACCORDING TO THE INVENTION

Example 1 was repeated except that 1-dodecanol (19.8 g) was used as the monoalcohol. A solution of an isocyanurate polyisocyanate having the following properties was obtained:
concentration—approx. 50%,
viscosity—800 mPa.s/23° C.,
NCO content—7.9%,
free diisocyanate—0.1%.

EXAMPLE 3 ACCORDING TO THE INVENTION

Example 1 was repeated except that 28.3 g 1-dodecanol were used instead of 19.8 g 2-ethyl hexanol and the quantity of butyl acetate was increased by 8.5 g. A solution of an isocyanurate polyisocyanate having the following properties was obtained:
concentration—approx. 50%,
viscosity—1100 mpa.s/23° C.,
NCO content—7.7%,
free diisocyanate—0.2%.

EXAMPLE 4 COMPARISON EXAMPLE

Example 1 was repeated except that methanol (4.8 g) was used as the alcohol and the solvent was reduced so that a 50% solution was again obtained. The isocyanurate polyisocyanate obtained had the following properties:
concentration—approx. 50%,
viscosity—1100 mpa.s/23° C.,
NCO content—7.8%,
free diisocyanate 0.28%.

EXAMPLE 5 COMPARISON EXAMPLE

Example 1 was repeated except that 19.8 g methanol were used. The isocyanurate polyisocyanate obtained had the following properties:
concentration—approx. 50%,
viscosity—1800 mpa.s/23° C.,
NCO content—6.7%,
free diisocyanate—0.2%.
The initially clear solution turned cloudy through the development of a precipitate after standing for about 8 days.

EXAMPLE 6 COMPARISON EXAMPLE

Example 1 was repeated except that there was no modification with alcohol and the diisocyanate was trimerized with no additions. Also, the solution was diluted with butyl acetate to 50%. The isocyanurate polyisocyanate obtained had the following properties:
concentration—approx. 50%,
viscosity—1500 mPa.s/23° C.,
NCO content—7.9%,
free diisocyanate—0.1%.

EXAMPLE 7 COMPARISON EXAMPLE, DE-OS 2 414 413

Example 6 was repeated except that 19.8 g 2-ethyl hexanol were added to the polyisocyanate solution obtained, followed by urethanization for 4 hours at 50° C. A clear solution was obtained. The isocyanurate polyisocyanate obtained had the following properties: concentration - approx. 50%,
viscosity—2800 mPa.s/23° C.,
NCO content—6.8%,
free diisocyanate—0.02%.
The solution of this polyisocyanate advantageously had a very low free diisocyanate content, but an unfavorably high viscosity and low NCO content.

EXAMPLE 8

Measurement of toluene compatibility

Procedure 15 to 20 g of the polyisocyanate solution were weighed out and toluene was added with stirring.

The test result is expressed as the quantity of toluene which caused the same degree of cloudiness as a standard solution (0.4 g canned milk containing 10% fat in 100 g water).

The results are shown in the following Table. Dilutability is expressed as the ratio between the toluene added and the quantity of isocyanate used.

TABLE

| Polyisocyanate solution (PIC) from Example | Quantity weighed out g | Addition ml toluene | ml Toluene g PIC |
|---|---|---|---|
| 1 | 16.381 | 40.46 | 2.47 |
| 2 | 17.941 | 53.39 | 2.53 |
| 3 | 16.735 | 48.69 | 2.91 |
| 4 | 15.963 | 19.95 | 1.25 |
| 5 | 17.452 | 20.07 | 1.15 |
| 6 | 18.725 | 23.03 | 1.23 |
| 7 | 19.223 | 25.95 | 1.35 |

The results demonstrate that the desired property, i.e., dilutability or compatibility with toluene, may only be optimally achieved with the products according to the invention. Compatability with other binder components and paint resins was also correspondingly improved.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a composition containing an isocyanurate polyisocyanate dissolved in a solvent inert to isocyanate groups which comprises
    a) reacting 2.5 to 7% of the isocyanate groups of a starting diisocyanate consisting essentially of 2,4-diisocyanatotoluene or a mixture of 2,4-diisocyanatotoluene and 2,6-diisocyanatotoluene with a monohydric alcohol corresponding to the formala

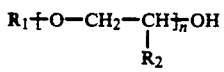

wherein
    $R_1$ is an aliphatic or cycloaliphatic $C_{6-18}$ hydrocarbon radical which may be olefinically unsaturated,
    $R_2$ is hydrogen or a methyl group, and
    n is 0 or an integer from 1 to 3,
    b) adding a sufficient amount of an organic solvent which is inert to isocyanate groups to form a 30 to 70% solution of the urethanized diisocyanate either before, during or after step a),
    c) subsequently partially trimerizing the remaining isocyanate groups of said urethanized diisocyanate in the presence of a catalyst which accelerates the trimerization of isocyanate groups and
    d) terminating the trimerization reaction when the content of unreacted diisocyananotoluene is less than 0.5% by weight by the addition of a catalyst poison.

2. The process of claim 1 wherein said monoalcohol comprises an alkanol which is free from ether groups, contains primary hydroxyl groups and has 8 to 12 carbon atoms in the alkyl radical.

3. The process of claim 1 wherein said monoalcohol comprises 2-ethyl hexanol.

4. The process of claim 1 wherein said starting diisocyanate consists essentially of a mixture of 2,4-diisocyanatotoluene with 2,6-diisocyanatotoluene in a weight ratio 2 to 9:1.

5. The process of claim 2 wherein said starting diisocyanate consists essentially of a mixture of 2,4-diisocyanatotoluene with 2,6-diisocyanatotoluene in a weight ratio 3:2 to 9:1.

6. The process of claim 3 wherein said starting diisocyanate consists essentially of a mixture of 2,4-diisocyanatotoluene with 2,6-diisocyanatotoluene in a weight ratio 3:2 to 9:1.

7. A composition containing an isocyanurate polyisocyanate dissolved in a solvent inert to isocyanate groups which is prepared by a process which comprises
    a) reacting 2.5 to 7% of the isocyanate groups of a starting diisocyanate consisting essentially of 2,4-diisocyanatotoluene or a mixture of 2,4-diisocyanatotoluene and 2,6-diisocyanatotoluene with a monohydric alcohol corresponding to the formala

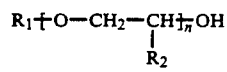

wherein
    $R_1$ is an aliphatic or cycloaliphati $C_{6-18}$ hydrocarbon radical which may be olefinically unsaturated,
    $R_2$ is hydrogen or a methyl group, and
    n is 0 or an integer from 1 to 3,
    b) adding a sufficient amount of an organic solvent which is inert to isocyanate groups to form a 30 to 70% solution of the urethanized diisocyanate either before, during or after step a),
    c) subsequently partially trimerizing the remaining isocyanate groups of said urethanized diisocyanate in the presence of a catalyst which accelerates the trimerization of isocyanate groups and
    d) terminating the trimerization reaction when the content of unreacted diisocyananotoluene is less than 0.5% by weight by the addition of a catalyst poison.

8. The composition of claim 7 wherein said monoalcohol comprises an alkanol which is free from ether groups, contains primary hydroxyl groups and has 8 to 12 carbon atoms in the alkyl radical.

9. The composition of claim 7 wherein said monoalcohol comprises 2-ethyl hexanol.

10. The composition of claim 7 wherein said starting diisocyanate consists essentially of a mixture of 2,4-diisocyanatotoluene with 2,6-diisocyanatotoluene in a weight ratio 2 to 9:1.

11. The composition of claim 8 wherein said starting diisocyanate consists essentially of a mixture of 2,4-diisocyanatotoluene with 2,6-diisocyanatotoluene in a weight ratio 2 to 9:1.

12. The composition of claim 9 wherein said starting diisocyanate consists essentially of a mixture of 2,4-diisocyanatotoluene with 2,6-diisocyanatotoluene in a weight ratio 2 to 9:1.

* * * * *